United States Patent [19]
Bogdanski et al.

[11] Patent Number: 5,830,202
[45] Date of Patent: Nov. 3, 1998

[54] ABSORBENT COMPRISING UPPER AND LOWER GEL LAYERS

[75] Inventors: Michael Scott Bogdanski; Barry Robert Feist, both of Cincinnati; John Joseph Litchholt, Harrison; Liza Marie Sanchez, Loveland, all of Ohio; Mattias Schmidt, Idstein, Germany

[73] Assignee: The Procter & Gamble Company, Cincinnati, Ohio

[21] Appl. No.: 776,372

[22] PCT Filed: Jul. 13, 1995

[86] PCT No.: PCT/US95/08709

§ 371 Date: Jan. 29, 1997

§ 102(e) Date: Jan. 29, 1997

[87] PCT Pub. No.: WO96/03947

PCT Pub. Date: Feb. 15, 1996

[30] Foreign Application Priority Data

Aug. 1, 1994 [EP] European Pat. Off. ............... 94111955

[51] Int. Cl.$^6$ .................................................. A61F 13/15
[52] U.S. Cl. ...................... 604/378; 604/385.1; 604/368
[58] Field of Search ................................... 604/368, 378, 604/385.1

[56] References Cited

U.S. PATENT DOCUMENTS

| | | |
|---|---|---|
| Re. 32,649 | 4/1988 | Brandt et al. . |
| 4,381,783 | 5/1983 | Elias . |
| 4,560,372 | 12/1985 | Pieniak . |

(List continued on next page.)

FOREIGN PATENT DOCUMENTS

| | | |
|---|---|---|
| 0 388 372 A1 | 9/1990 | European Pat. Off. . |
| 0 640 330 A1 | 12/1993 | European Pat. Off. . |
| 0 631 768 A1 | 1/1995 | European Pat. Off. . |
| 0 695 541 A1 | 2/1996 | European Pat. Off. . |
| 0 700 672 A | 3/1996 | European Pat. Off. . |
| 0 700 673 A1 | 3/1996 | European Pat. Off. . |
| 0 705 587 A2 | 4/1996 | European Pat. Off. . |
| 2636899 | 3/1977 | Germany . |
| 2208477 | 4/1989 | United Kingdom . |
| 2286832 | 8/1995 | United Kingdom . |
| 2296438 | 7/1996 | United Kingdom . |
| 92/11831 | 7/1992 | WIPO . |
| 94/02092 | 2/1994 | WIPO . |
| 94/07546 | 4/1994 | WIPO . |
| 95/10995 | 4/1995 | WIPO . |
| 95/11651 | 5/1995 | WIPO . |
| 95/11652 | 5/1995 | WIPO . |
| 95/11653 | 5/1995 | WIPO . |
| 95/11654 | 5/1995 | WIPO . |
| 95/21596 | 8/1995 | WIPO . |
| 96/03947 | 2/1996 | WIPO . |

*Primary Examiner*—John G. Weiss
*Assistant Examiner*—Dennis Ruhl
*Attorney, Agent, or Firm*—Carl J. Roof; E. Kelly Linman; Jacobus C. Rasser

[57] ABSTRACT

The invention relates to an absorbent structure (1) having a first layer which forms a mixture of absorbent gelling material particles (5), fibers, a second layer comprising liquid permeable substrate (7), and absorbent gelling material particles (9) attached to said substrate thus forming a laminate. The weight of the absorbent gelling material particles (5) in the mixed layer is not more than 70 percent, preferably not more than 60 percent of the weight of the mixed layer. The combined weight of the absorbent gelling material particles attached to the substrate (7), and in the mixed layer (5) is at least 80 percent, preferably at least 140 percent of the weight of fibers in the mixed layer (5). The laminate (7, 9) can be located on top of the mixed layer (5), and comprises an acquisition zone (15) of low basis weight of absorbent gelling material particles. The laminate may also be located below the mixed layer.

27 Claims, 7 Drawing Sheets

U.S. PATENT DOCUMENTS

| | | |
|---|---|---|
| 4,610,678 | 9/1986 | Weisman et al. . |
| 4,781,711 | 11/1988 | Houghton et al. . |
| 4,790,839 | 12/1988 | Ahr . |
| 4,973,325 | 11/1990 | Sherrod et al. . |
| 4,988,344 | 1/1991 | Reising et al. . |
| 4,988,345 | 1/1991 | Reising . |
| 5,087,506 | 2/1992 | Palumbo . |
| 5,147,345 | 9/1992 | Young et al. . |
| 5,294,478 | 3/1994 | Wanek et al. . |
| 5,300,053 | 4/1994 | Genaro . |
| 5,300,054 | 4/1994 | Feist et al. . |
| 5,304,161 | 4/1994 | Noel et al. . |
| 5,387,207 | 2/1995 | Dyer et al. . |
| 5,411,497 | 5/1995 | Tanzer et al. . |
| 5,425,725 | 6/1995 | Tanzer et al. . |
| 5,433,715 | 7/1995 | Tanzer et al. . |
| 5,440,061 | 8/1995 | Gibson . |
| 5,454,800 | 10/1995 | Hirt et al. . |
| 5,466,513 | 11/1995 | Wanek et al. . |
| 5,509,915 | 4/1996 | Hanson et al. . |

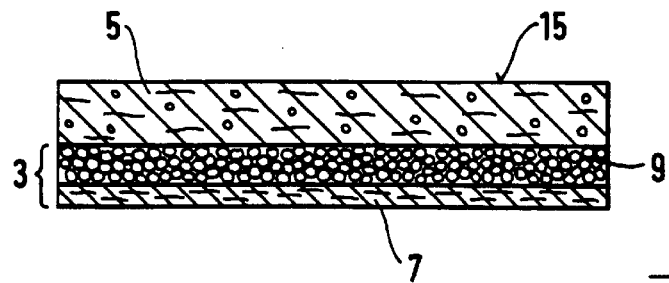
Fig. 4
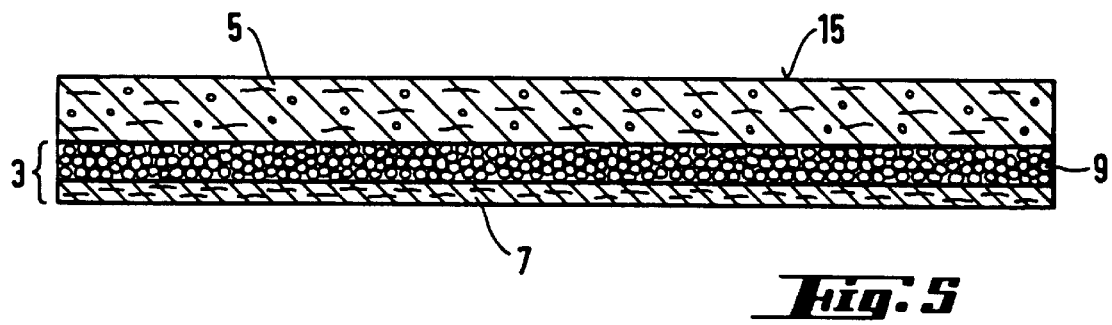
Fig. 5
Fig. 6
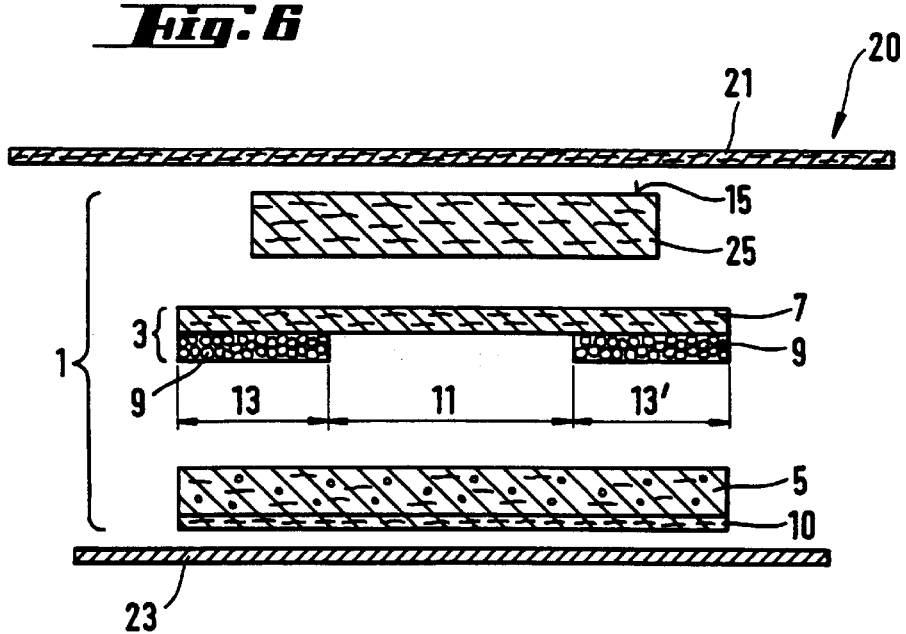

ABSORBENT COMPRISING UPPER AND LOWER GEL LAYERS

FIELD OF THE INVENTION

The invention relates to an absorbent structure comprising an upper layer and a lower layer, each layer comprising absorbent gelling material particles.

The invention also relates to an absorbent structure comprising an upper layer and a lower layer, each layer comprising absorbent gelling material particles, the upper layer comprising an acquisition zone and a storage zone, the average basis weight of absorbent gelling material particles in the acquisition zone being lower than the average basis weight of the absorbent gelling material particles in the storage zone, wherein the lower layer comprises a mixture of absorbent gelling material particles and fibers.

The invention furthermore relates to a method for making such an absorbent structure.

BACKGROUND OF THE INVENTION

From WO 94/02092 (Coles) a sanitary napkin is known having a core which is comprised of a layer of absorbent gelling material sandwiched between two tissue layers. The layer of absorbent gelling material has a central acquisition zone that is substantially free of absorbent gelling material. The central acquisition zone serves to promote longitudinal spread of liquids along the sanitary napkin's core and to reduce side soiling.

U.S. Pat. No. 5,304,161 discloses a multilayer absorbent structure having an upper layer comprising absorbent gelling material and a lower storage layer of absorbent gelling material. A liquid passage way is provided in the upper layer of absorbent gelling material such that the upper and lower layers are in fluid communication. The upper layer may be comprised of two separate strips of absorbent gelling material.

U.S. Pat. Nos. 4,988,344 and 4,988,345 (Reising) and WO92/11831 (Feist) disclose absorbent articles having an upper layer comprising absorbent gelling material overlying a lower layer of absorbent gelling material. A liquid acquisition aperture is provided in the upper layer.

From DE-A-26 36 899 (Unilever) a multilayer sanitary napkin is known comprising three layers of absorbent gelling material. Each layer of absorbent gelling material is sandwiched between two tissue layers. The layers of absorbent gelling material are attached to the tissue layers in a striped pattern to promote longitudinal spread of liquids and to improve vertical uptake of liquid into the lower layers of the sanitary napkin.

In absorbent articles that comprise a mixture of absorbent gelling material particles and fibers, as described in U.S. Pat. No. 4,610,678 (Weisman), it has been found that at relatively high concentrations of absorbent gelling material particles, for instance above about 60% by weight of the mixture, the particles tend to separate from the fibers and collect in the lowest point of the absorbent structure. This has the undesirable effect that in the parts of the absorbent structure from which the particles have separated, insufficient absorbent capacity is present, and that liquids can be squeezed out of these parts. On the other hand, the absorbent efficiency and liquid-handling properties of the absorbent structure are reduced in those areas where the absorbent gelling material particles have collected and where very high local concentrations and basis weights of particles are present.

Furthermore, during formation of absorbent products having a relatively high concentration of absorbent gelling particles mixed into the fiber matrix, the particles that separate from the fiber matrix can contaminate the diaper forming equipment, especially the laydown screens on which the absorbent structures are formed, but also other equipment such as for instance the knifes for cutting side notches in the topsheet and backshet of an absorbent product.

Another negative effect of relatively high concentrations of absorbent gelling material, is that so called 'gel blocking' may occur. When the absorbent gelling material particles swell upon being wetted, they will expand into the void spaces between the fibers and will form a resistance for liquids flowing into the absorbent core. On the other hand, a high concentration of absorbent gelling material in the absorbent product is desirable to effectively contain the absorbed liquids and to prevent these liquids from travelling back to the topsheet of the absorbent product. Problems with gel blocking of the absorbent gelling materials have been reduced by varying the chemical composition of the absorbent gelling materials, such as for instance disclosed in U.S. application Ser. No. 08/219066 (Goldman) filed on Mar. 29, 1994 or in U.S. Pat. No. Re. 32,649 (Brandt). However, increased resistance of the absorbent gelling materials to gel blocking is often gained at a cost of reduced absorbent capacity of such absorbent gelling materials.

It is an object of the present invention to provide an absorbent structure comprising a mixture of absorbent fibers and a relatively large amount of absorbent gelling material.

It is a further object of the invention to provide an absorbent structure wherein the position of the absorbent gelling material, in its dry state, is fixed during production and use.

It is another object of the present invention to provide an absorbent structure which effectively absorbs liquids without adverse effects of gel blocking.

It is again another object of the invention to provide an absorbent structure which has a relatively low caliper and a sufficient theoretical average basis capacity.

It is again a further object of the invention to provide an absorbent structure that allows rapid acquisition of liquids deposited onto the structure and which remains permeable to liquids in its wet state.

It is also an object of the invention to provide an absorbent structure which stores liquids away from the user and which maintains a dry user-facing side.

It is another object of the invention to provide a method of making an absorbent structure wherein the position of the absorbent gelling material can be easily controlled and wherein contamination by loose absorbent gelling material particles is reduced.

SUMMARY OF THE INVENTION

An absorbent structure according to the invention comprises an upper layer having a substrate and absorbent gelling material particles attached to said substrate. Below the substrate, a lower layer is positioned which lower layer comprises a mixture of fibers and absorbent gelling material particles. In the upper layer an acquisition zone is provided which comprises a relatively low average basis weight of absorbent gelling material particles, the acquisition zone preferably being free of absorbent gelling material particles. Through the acquisition zone, liquids will be able to quickly enter into the absorbent structure where they can be absorbed by the lower layer which functions as a storage layer.

The weight of the absorbent gelling material particles in the mixed lower layer is not more than 70%, preferably not more than 60% of the weight of the mixed lower layer, the combined weight of absorbent gelling material particles in the upper layer and the mixed lower layer being at least 80 percent, preferably at least 140 percent of the weight of fibers in the mixed lower layer.

By attaching a number of absorbent gelling material particles to a substrate in a separate layer overlying the lower layer of mixed fibers and absorbent gelling material, a high total concentration of absorbent gelling material particles can be achieved in the absorbent structure. By positioning part of the absorbent gelling material particles in the upper layer, the concentration of the absorbent gelling material particles in the mixed layer can remain at a low enough level at which bonding of the majority of the particles in their dry state in the fiber matrix is still possible. Hence sifting of the absorbent gelling material particles from the lower layer is prevented while maintaining a sufficiently high amount of absorbent gelling material in the absorbent structure to obtain a sufficient absorbent capacity per unit area (also called "average basis capacity").

Attachment of the particles to the substrate in the upper layer prevents migration of the absorbent gelling material particles from that layer and accurately fixes the horizontal and vertical position of the absorbent gelling material particles in the absorbent structure. By attaching the particles to the substrate, they can be positioned in the upper part of the mixed layer of fibers and particles, without sifting under the influence of gravity to the bottom or to the end parts of the mixed layer.

The presence of the layer of absorbent gelling material particles on the user-facing side of the structure, will help in maintaining a dry user side and prevents liquids from migrating back to the user. To prevent liquid from pooling on top of the upper layer of absorbent gelling material particles, the acquisition zone is provided in the layer of particles. Through the acquisition zone liquids are able to quickly enter into the absorbent structure. The presence of the acquisition zone ensures that gushes of liquids are rapidly absorbed and prevents the gushes from flowing off the user facing side of the absorbent structure and from causing soiling. Due to the relatively low concentration of absorbent gelling material particles in the mixed layer, the liquids can be absorbed by that layer without negative effects of gel blocking.

Furthermore, during formation of the absorbent structure, the layer comprising the mixture of fibers and absorbent gelling material particles can be formed substantially without absorbent gelling material particles sifting out of this layer. During formation of an absorbent article comprising an absorbent structure according to the invention, vigorous movement of the mixed layer takes place, for instance on lay-down of the fibers and absorbent gelling material particles, on folding or during the packing stage. During these operations it is essential that the absorbent gelling material particles remain immobilised both for the mixed layer and for the substrate layer of the absorbent structure.

In the process of forming an absorbent structure according to the invention, the absorbent gelling material particles in the mixed layer are attached to the fibers in their dry state at relatively low concentrations. To the substrate layer, the absorbent gelling material particles are attached for instance by wet compression or adhesive attachment. Alternatively, the absorbent gelling material particles that are attached to the substrate can be mutually connected by interparticle crosslink bonds, as described in U.S. Pat. No. 5,180,622 (Berg), U.S. Pat. No. 5,102,597 (Roe et al), and U.S. application Ser. No. 07/955635 (Rezai) and can be connected to the substrate by an interparticle crosslink agent as described in U.S. application Ser. No. 08/142258 (Hseuh). The layer comprising the substrate and the absorbent gelling material particles may be formed during the production process of an absorbent article, or may be preformed and may be supplied during the production process of an absorbent article from a storage roll. The mixed layer and the substrate carrying the particles are combined to form the absorbent structure.

In the mixed layer of fibers and absorbent gelling material particles, the particles can be distributed uniformly throughout the layer, or may be distributed at concentrations which vary throughout the thickness of the layer, as for instance described in EP-A-0 198 683 (Duenk). Preferably the mixed layer forms at least a part of a continuous matrix of airlaid fibers, the lower part of which is substantially free of absorbent gelling material particles. Such a lower part of the fibrous matrix, substantially free of absorbent gelling material particles is also referred to as a "dusting layer" and is used in absorbent structures which are made by airlaying, to prevent the absorbent gelling material particles from contaminating the laydown screen.

The concentration of absorbent gelling material in the "mixed layer" may vary along the horizontal dimensions of the mixed layer. For instance, the concentration of the absorbent gelling material particles may be varied along the length of the mixed layer to tailor the absorbent structure to users of a specific gender. Furthermore, the concentration of the particles may also vary along the dimension of the transverse center line (the width) of the mixed layer to provide an acquisition zone in the mixed layer.

For the purpose of the present invention, "the mixed layer" is defined as the volume of a fibrous matrix comprising both fibers and a substantially non-zero amount of absorbent gelling material particles. The "mixed layer" excludes the dusting layer and other layers in which no absorbent gelling material particles are comprised.

The average basis weight of the absorbent gelling particles that are connected to the substrate in the storage zone is at least 25 g/m$^2$, preferably at least 40 g/m$^2$. The average basis weight of the absorbent gelling particles in the acquisition zone is lower than 25 g/m$^2$, and is preferably substantially zero.

With "average basis weight" of the absorbent gelling material particles in the acquisition zone or in the storage zone, is meant the total amount of absorbent gelling material particles in each zone, divided by the surface area of the zone.

The acquisition zone is preferably formed by a stripe of about 2 to 5 cm in width, but can be of oval or rectangular shape, or can comprise a number of circles, squares or any other pattern.

An alternative embodiment of an absorbent structure according to the invention is characterised in that the mixed layer of fibers and particles overlies a lower layer, the lower layer comprising a substrate to which the absorbent gelling material particles are attached. In this case, the layer of particles in the lower layer can be homogeneously distributed across the surface of the substrate, or can comprise an acquisition zone or a striped pattern. A high concentration of absorbent gelling particles in the lower layer of the absorbent structure will retain liquids at the position which is furthest from the wearer in use. The substrate can act as a cushioning layer between the absorbent gelling material particles and a liquid impermeable backsheet that can be used in combination with the absorbent structure, so that the absorbent gelling material particles do not penetrate through the backsheet.

Again alternatively, the mixed layer can be encased between an upper substrate and a lower substrate, each substrate comprising absorbent gelling material particles. The substrates of the upper and lower layer can be separate materials, or can be formed by a single piece of material, which is wrapped around the mixed layer of fibers and particles.

The absorbent structure according to the invention can be made of a surprisingly small caliper while still maintaining a sufficient absorbent average basis capacity of at least 0.5 ml/cm$^2$, preferably at least 0.6 ml/cm$^2$. A test for measuring the basis capacity has been described in detail in European patent application no. 93305150.0 (attorney's docket CM 580) and in European application no. 93309614.1 (attorney's docket CM 643). In the test described in the earlier mentioned European patent applications, the absorbent capacity is measured for a multilayer structure. For each layer separately, the amount of liquid (in grams) is determined that is absorbed per unit area of the layer. The absorbent capacity of the whole multilayer structure is given by the sum of the absorbent capacities of each individual layer, and is because of this summation of separately measured basis capacities also referred to as the "theoretical average basis capacity".

The caliper of the absorbent article comprising the absorbent structure according to the invention is below 8.4 cm (3.3 inch) in a stack height test, wherein 10 bi-folded absorbent structures are compressed under a load 800 kg for 3 seconds. The stack height test has been described in detail in European application number 93305150.0.

BRIEF DESCRIPTION OF THE DRAWINGS

The invention will be described in detail with reference to the accompanying drawings. In the drawings:

FIG. 6 shows a schematic transverse cross-sectional view of an absorbent article comprising an absorbent structure according to the invention which includes a dusting layer.

DETAILED DESCRIPTION OF THE INVENTION

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. A preferred embodiment of an absorbent article of the present invention is the unitary disposable absorbent article, diaper 20, shown in FIG. 7. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, training pants, pull-on diapers, feminine hygiene garments such as sanitary napkins, and the like.

Figure 1:
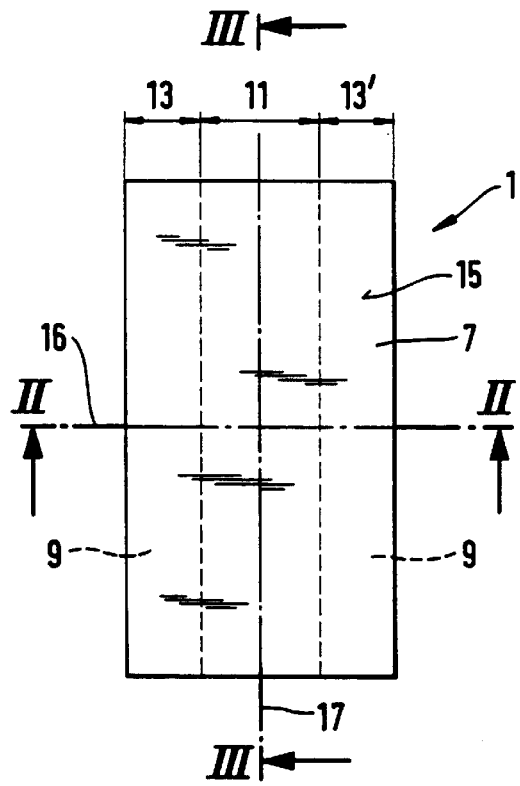
FIG. 1 shows a top view of an absorbent structure according to the invention.
Figure 2:
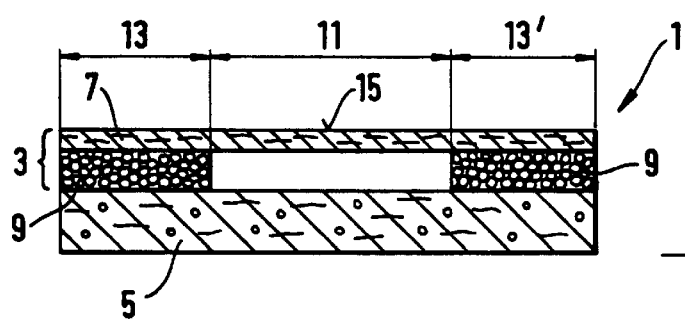
FIGS. 2 and 3 respectively show a transverse cross-sectional view and a longitudinal cross-sectional view of the absorbent structure of FIG. 1, wherein the laminate is positioned at the user-facing side of the absorbent structure, FIGS. 4 and 5 respectively show a transverse cross-sectional view and a longitudinal cross-sectional view of the absorbent structure of FIG. 1, wherein the laminate is positioned at the backsheet-facing side of the absorbent structure.
Figure 3:
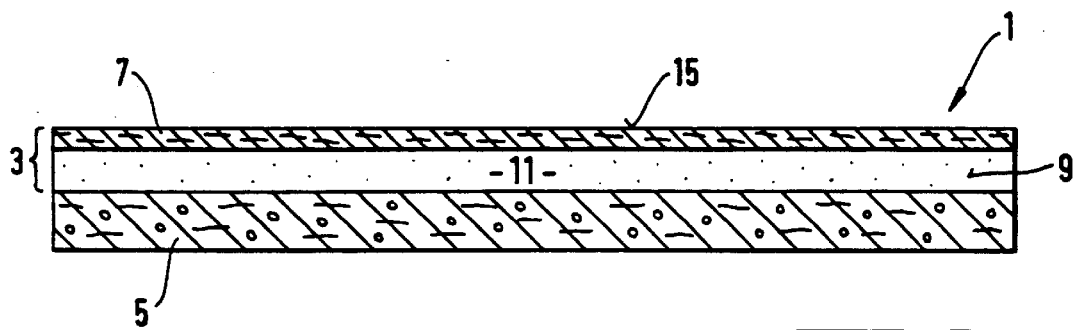

FIG. 1 shows a plan view of an absorbent structure 1, comprising storage zones 13,13' and central acquisition zone 11. FIGS. 2 and 3 show a cross-sectional view of the absorbent structure 1 along the transverse center line 16 and the longitudinal center line 17 respectively. The absorbent structure comprises an upper layer 3 and a lower layer 5. The upper layer 3 comprises a substrate 7 and a layer of absorbent gelling material particles 9 attached to the substrate 7. The combination of the substrate 7 and the absorbent gelling material particles attached thereto is also referred to as a "laminate". The upper layer 3 comprises a central acquisition zone 11 and a storage zone 13,13' bordering the acquisition zone 11 on either side. The average basis weight of the absorbent gelling material particles 7 in the acquisition zone is relatively low compared to the average basis weight of the absorbent gelling material particles in the storage zone 13,13'. Preferably no absorbent gelling material particles are comprised in the acquisition zone 11. The storage zone 13,13' can comprise an average basis weight of absorbent gelling material particles of more than 25 g/m$^2$, preferably more than 40 g/m$^2$, the average basis weight of the particles in the acquisition zone 11 being below 25 g/m$^2$.

The lower layer 5 comprises a mixture of absorbent gelling material particles and fibers, which may be cellulose fluff pulp, synthetic fibers, or combinations thereof. The lower layer 5 is preferably formed by air laying. The upper layer 3 is preferably placed on top of the lower layer 5 in such a manner that the absorbent gelling material particles 9 are comprised between the substrate 7 and the lower layer 5. The substrate 7 prevents the absorbent gelling material particles, if they become detached from the substrate, to migrate to the user-facing side 15 of the structure 1 and prevents the particles from contacting the skin of the user.

FIGS. 4 and 5 show cross-sectional views along the transverse centerline 16 and the longitudinal center line 17 of an embodiment of the absorbent structure wherein the laminate 3 is located below the mixed layer 5. The layer of absorbent gelling material particles 9 is uniformly distributed across the substrate 7. When desired, stripes, channels or other variations in the basis weight of the absorbent gelling material particles in the laminate 3 may be applied.

FIG. 6 shows a schematic cross-sectional view of a preferred embodiment of an absorbent article 20 comprising an absorbent structure 1 according to the invention. The absorbent structure 1 is encased between a liquid permeable topsheet 21 and a liquid-impermeable backsheet 23.

The topsheet

The topsheet 21 is positioned adjacent the body-facing surface 15 of the absorbent structure, or core, 1 and is preferably joined thereto and to the backsheet 23 by attachment means (not shown) such as those well known in the art. Suitable attachment means are described with respect to joining the backsheet 23 to the absorbent structure 1. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 21 and the backsheet 23 are joined directly to each other in the periphery of the absorbent article 20 and are indirectly joined together by directly joining them to the absorbent structure 1 by the attachment means (not shown).

The topsheet 21 is compliant, soft feeling, and non-irritating to the wearer's skin. Further, the topsheet 21 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 21 is made of a hydrophobic material to isolate the wearer's skin from liquids contained in the absorbent core 1. Preferably the topsheet is coated with a hydrophilic coating which is washed off the topsheet after being wetted. There are a number of manufacturing techniques which may be used to manufacture the topsheet 21. For example, the topsheet 21 may be a nonwoven web of fibers spunbonded, carded, wet-laid, meltblown, hydroentangled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The Backsheet

The backsheet 23 is positioned adjacent the garment surface of the absorbent structure 1 and is preferably joined thereto by attachment means (not shown) such as those well known in the art. For example, the backsheet 23 may be secured to the absorbent structure 1 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986, more preferably several lines of adhesive filaments swirled into a spiral pattern such as is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 23 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 23 prevents the exudates absorbed and contained in the absorbent structure 1 from wetting articles which contact the absorbent article 20 such as bedsheets and undergarments. The backsheet 23 may thus comprise a woven or nonwoven material, polymeric films such as thermoplastic films of polyethylene or polypropylene, or composite materials such as a film-coated nonwoven material. Preferably, the backsheet is a thermoplastic film having a thickness of from about 0.012 mm (0.5 mil) to about 0.051 mm (2.0 mils). Particularly preferred materials for the backsheet include RR8220 blown films and RR5475 cast films as manufactured by Tredegar Industries, Inc. of Terre Haute, Ind. The backsheet 23 is preferably embossed and/or matte finished to provide a more clothlike appearance. Further, the backsheet 23 may permit vapors to escape from the absorbent structure 1 (i.e., breathable) while still preventing exudates from passing through the backsheet 23.

The Acquisition Layer

In the embodiment of FIG. 6, the absorbent structure 1 comprises an upper acquisition layer 25. The acquisition layer 25 serves to quickly collect large gushes of liquids and to isolate these from the body of the wearer until these liquids have been absorbed in the underlying layers 5,7,9. The density of the acquisition layer 25 is preferably between 0.02 and 0.13 g/cm$^3$, the basis weight being between 50 and 500 g/m$^2$, depending on the volume of the gush that is to be taken up. A preferred material for the acquisition layer 25 is chemically stiffened cellulose material as described in EP-A-0 429 112 (Herron) U.S. Pat. No. 4,898,642 (Moore) and 4,889,597 (Bourbon). Further useful acquisition layers comprise open networks of thermally bonded air laid synthetic fibers, also referred to as "TBAL", as described in U.S. application Ser. No. 08/141,156 and EP-A- 513 148. Other useful materials for use as an acquisition layer are described in PCT application no. PCT/EP94/01814, filed on Jun. 3, 1994.

An important property of the acquisition layer 25 is its ability to maintain a sufficient void volume for liquid uptake, even when wet. The fibers in the layer 25 should be sufficiently resilient to not collapse in their wet state upon compression. It was found that layers having a wet compressibility of at least 5 cm$^3$g$^{-1}$ and a drip capacity of at least 10 gg$^{-1}$ can be successfully used 3in acquisition layer 25.

The wet compressibility and the drip capacity can be measured by the test described in detail in European application no. 93305150.0 and described in detail in the Test Method section below.

Further suitable materials for the acquisition layer are airfelt, mixtures of airfelt and synthetic fibers or for instance high loft nonwovens such as produced by Corovin GmbH, Postfach 1107, D-31201 Peine, Germany under the tradename COROLOFT.

The laminate

The substrate layer 7 of the laminate 3 can for example be formed by a nonwoven layer or by a tissue layer such as BOUNTY tissue as marketed by the Procter & Gamble Company, or such as a high wet-strength tissue of a basis weight of 22.5 g/m$^2$ as produced by STREPP GmbH & Co, KG, D 5166 Kreuzau-Untermaubach, Germany, under the reference NCB. Alternatively, the substrate layer 7 is formed by a three-dimensional apertured thermoplastic film as described in EP-A-0 203 820 (Curro), EP-A- 0 156 471 (Curro) and EP-A- 0 141 654 (Koger II). Other suitable materials for forming the substrate layer 7 are high wet-strength nonwovens, such as polyolefin nonwovens.

The absorbent gelling material particles can be attached to the substrate by applying a layer of adhesive to the substrate 7, followed by deposition of the particles onto the layer of adhesive. Preferably no adhesive is applied to the acquisition zone 11 of the substrate 7, so that no particles are attached in that area. A relatively small amount of adhesive may however be applied to the acquisition zone to attach this zone to the underlying mixed layer for improvement of the integrity of the absorbent structure. A suitable adhesive is for instance hotmelt adhesive as produced by Findley, Roosendaal, the Netherlands under the reference H 2127. The adhesive can be deposited as a melt-blown film which is blown at such high air speeds that the film breaks up into an open network of filaments as described in U.S. Pat. No. 4,573,986 (Minetola). Alternatively, a spiral pattern of adhesive may be deposited to obtain a liquid-permeable network of adhesive filaments as described in U.S. Pat. Nos. 3,911,173, 4,031,854, and 4,098,632 (all issued to Sprague).

In a preferred embodiment, the absorbent gelling material paritlces are directed through a stream of adhesive prior to contacting the substrate to form adhesively coated particles. Subsequently, the adhesively coated particles are deposited onto the substrate. In this way liquid good liquid permeability of the laminate is maintained, and very little blocking of liquid by the adhesive takes place.

It is also possible to bond the absorbent gelling material particles without the use of an adhesive. The particles can be deposited onto a moist substrate 7 such that the particles absorb moisture on their surfaces and become tacky. Subsequent drying of the moist substrate 7 under application of pressure, results in attachment of the particles 9 to the substrate 7.

In case the particles are interconnected by application of an interparticle crosslink agent to form an interpartically crosslinked aggregate, the absorbent gelling material particles may be bonded to the substrate by the interparticle crosslink agent. This has been described in detail in U.S. application Ser. No. 081142258 (Hseuh).

A method of forming a multilayer laminate having a multiplicity of tissue layers and layers of absorbent gelling material particles encased between the tissue layers, is described in U.S. Pat. No. 4,578,068 (Kramer). In this structure, the absorbent gelling material particles are bonded to the tissue layers substantially entirely by fiber entrapment. A method for depositing absorbent gelling material particles onto a substrate has been described in U.S. Pat. No. 4,551,191 (Kock).

Preferably, the basis weight of the particles 9 in the storage zone 13,13' is above 25 g/m$^2$. In a preferred baby diaper 1, the laminate 3 of the absorbent structure comprises a total of between 1 and 4 grams of absorbent gelling material particles, such that the combined weight of the absorbent gelling material particles in the laminate 3 and in the mixed layer 5 forms at least 40% of the weight of the fibers in the mixed layer 5.

In the acquisition zone 11, preferable no absorbent gelling material particles are present. Upon application of the absorbent gelling material particles to the substrate 7, the acquisition zone 11 can be maintained free of adhesive by selective application of adhesive to the substrate for instance by application of two parallel stripes of adhesive covering the acquisition zones 13,13'. The adhesive can be applied by two separate glue nozzles, or can be applied by a single nozzle via a shielding element which blocks the part of the glue stream that is directed to the acquisition zone 11. After depositing the absorbent gelling material particles onto the adhesively coated substrate 7, the particles can be removed from the acquisition zone 11 that does not comprise any adhesive by directing an airstream onto the particles or by shaking of the substrate 7 such that the undetached particles fall off the substrate.

Figure 8:
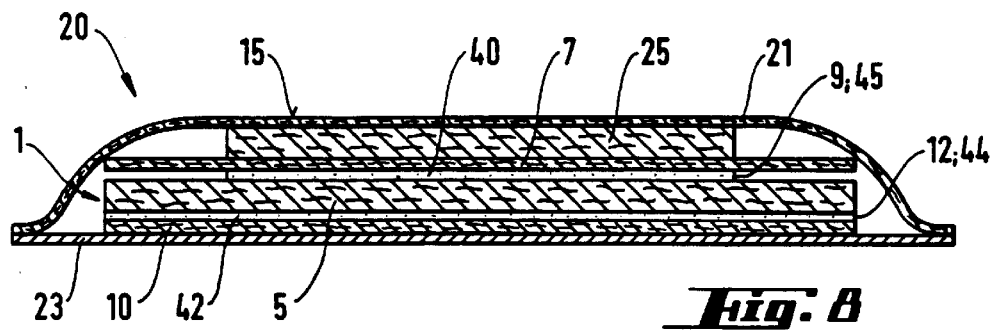
FIG. 8 shows a longitudinal cross-sectional view of an embodiment of an absorbent article comprising an absorbent structure.
Figure 9:
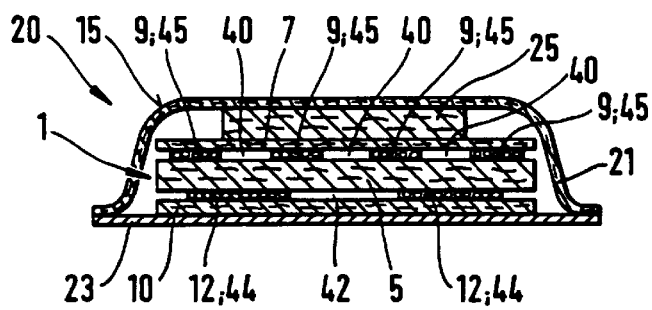
FIG. 9 shows a transverse cross-sectional view of the absorbent article of FIG. 8.
Figure 10:
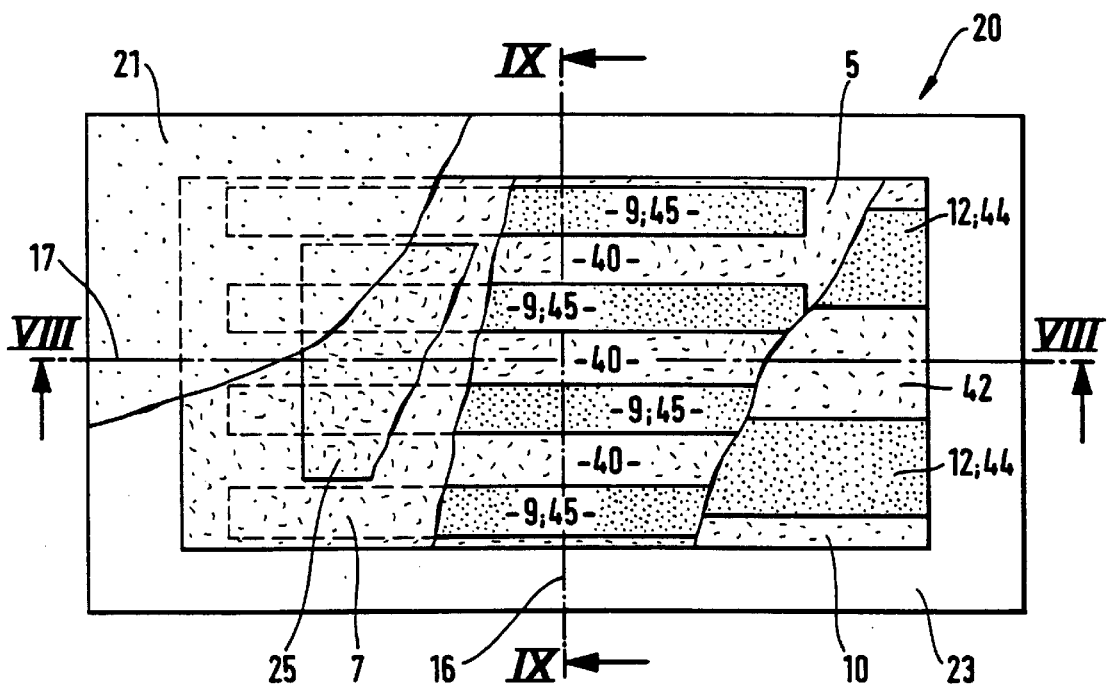
FIG. 10 shows a top view of the absorbent article of FIGS. 8 and 9, FIGS. 11 to 14 show transverse cross-sectional views of further embodiments of absorbent structures according to the invention, and FIG. 15 schematically shows a production line for forming absorbent articles comprising an absorbent structure according to the invention.

The acquisition zone 11 may be formed by any pattern of open areas such as a number of channels or a number of circles, squares etc. As is shown in FIGS. 8, 9 and 10, the absorbent gelling material particles can be attached to the substrate 7 in a number of short stripes 45. The application of the adhesive for attaching the absorbent gelling material particles, and the deposition of the absorbent gelling material particles onto the substrate can be effected by an intermittent operation of the glue nozzle and the absorbent gelling material applicator (pulsed operation).

The mixed layer

The mixed layer 5 may comprise any absorbent fibrous means which is generally compressible, conformable, non-irritating to the wearer's skin, and capable of absorbing and retaining liquids such as urine and other certain body exudates. The lower layer 5 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials which may be used in addition to the fibrous material included in the layer 5 are for instance creped cellulose wadding; meltblown polymers including coform; chemically stiffened, modified or cross-linked cellulosic fibers; tissue including tissue wraps and tissue laminates; absorbent foams; absorbent sponges, etc. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent structure 1 should, however, be compatible with the design loading and the intended use of the diaper 20. Further, the size and absorbent capacity of the absorbent structure 1 may be varied to accommodate wearers ranging from infants through adults. Exemplary mixed layers 5 are described in U.S. Pat. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference.

In the embodiment as depicted in FIG. 6, a fibrous layer 10 that is substantially free of absorbent gelling material particles, also referred to as a "dusting layer", is located underneath the mixed layer 5. The dusting layer 10 and the fibrous matrix of the mixed layer 5 may be parts of a single homogeneous fibrous layer which has been formed by airlaying. However, for the purpose of the present invention, the dusting layer 10 is not considered as a part of the mixed layer 5. Forming an absorbent core comprising a mixed layer 5 and a dusting layer 10 has been described in U.S. Pat. No. 4,888,231 entitled "Absorbent Core Having A Dusting Layer" issued to Angstadt on Dec. 19, 1989.

The absorbent gelling material particles can be homogeneously distributed throughout the thickness of the mixed layer 5. Alternatively, the mixed layer 5 may comprise a mixture of fibers and absorbent gelling material particles, more than 70% by weight of the absorbent gelling material in the layer 5 being located in the lower half of said layer. Such a gradient of density of absorbent gelling material particles is described in EP-A- 0 198 683 (Duenk).

The total amount of airfelt comprised in the mixed layer 5 and the dusting layer 10, is for baby diapers suitable for babies between 9 and 18 kg, typically between 12 g and 23 g, preferably between 16 g and 18 g. In an embodiment of the absorbent structure as typically used in baby diapers, the mixed lower layer 5 typically comprises a mixture of between 8 and 12 grams of absorbent gelling material particles blended with between 16 and 18 grams of airfelt, such that the weight of the absorbent gelling material particles forms between 31% and 43% of the total weight of the mixed lower layer 5. It is however possible to use lower amounts of absorbent gelling material particles in the mixed layer, which may contain 6 g or less of absorbent gelling material particles.

For the laminate 3 and the mixed layer 5, the weight of the absorbent gelling material particles may vary along the length or the width of the lamiate 3 or mixed layer 5. For instance, in an absorbent diaper especially adapted for boys, the majority of the absorbent gelling material may be located in the front half part of the laminate 3 and/or mixed layer 5. For diapers especially adapted for girls, the majority of the absorbent gelling material particles may be located in the two central quadrants located around the transverse centerline 16 in FIG. 1 of the laminate and/or mixed layer.

Also may the concentration of absorbent gelling material particles in the mixed layer be lower along a central longitudinal zone and higher along two longitudinal zones alongside the central zone, similar to the profile as shown in FIG. 1. In this way, an extra acquisition zone for liquid uptake and -transport is provided in the mixed layer.

The absorbent article

Figure 7:
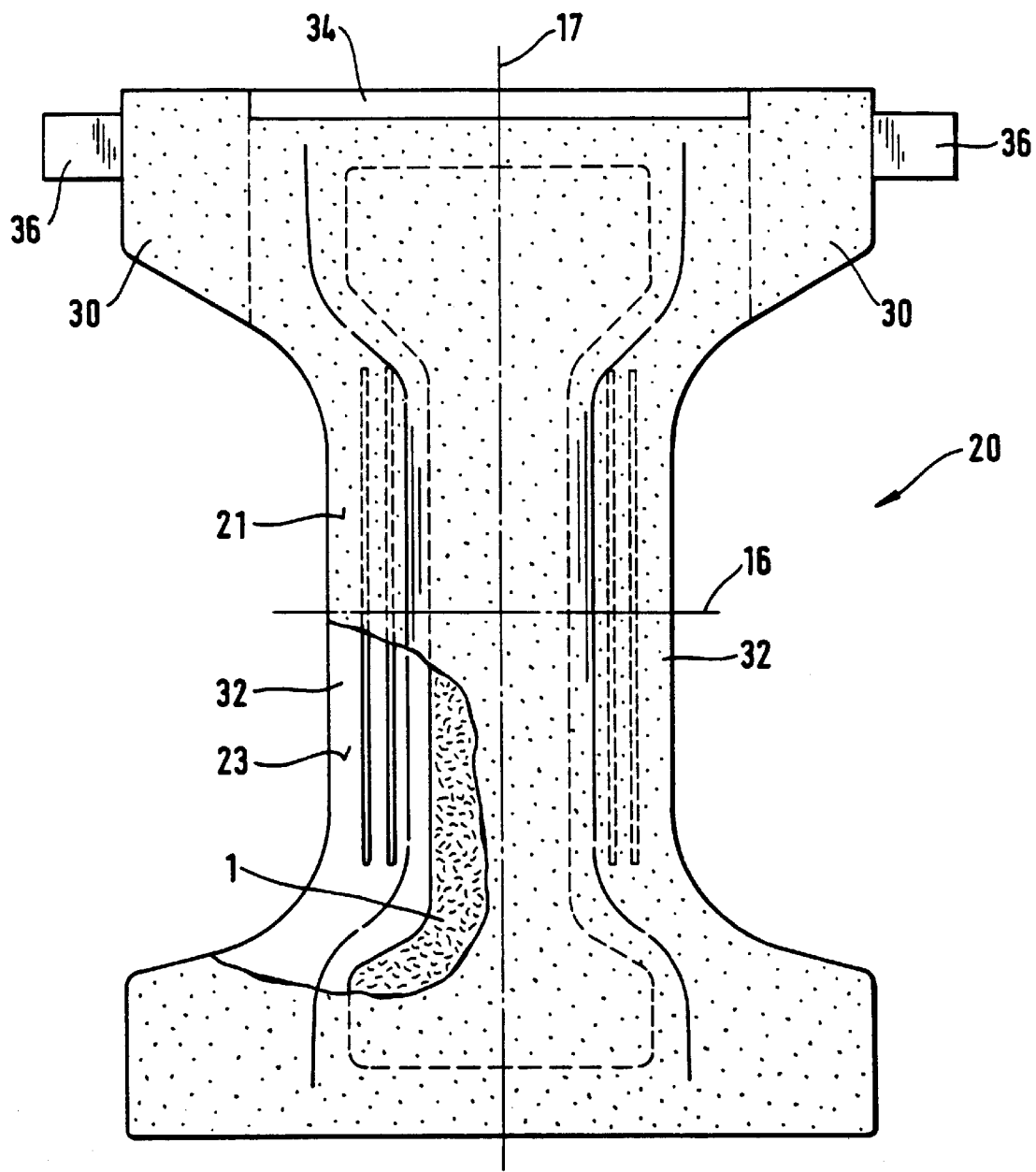
FIG. 7 shows a partially cut-away plan view of an absorbent article.

FIG. 7 is a plan view of the absorbent article 20, in particular a diaper, of the present invention in its flat-out, uncontracted state (i.e., with elastic induced contraction pulled out) with portions of the structure being cut-away to more clearly show the construction of the diaper 20 and with the portion of the diaper 20 which faces or contacts the wearer, the inner surface, oriented towards the viewer. As shown in FIG. 7, the diaper 20 comprises a liquid pervious topsheet 21 of which a part has been cut away to show the underlying structure. The core 1 is comprised between the topsheet 21 and backsheet 23. The diaper 20 further comprises elasticized side panels 30 which can elastically extend in the direction of the transverse center line 16, elasticized leg cuffs 32; an elastic waist feature 34; a fastening system generally multiply designated as 36;

FIG. 7 shows a preferred embodiment of the diaper 20 in which the topsheet 21 and the backsheet 23 have length and width dimensions generally larger than those of the absorbent structure 1. The topsheet 21 and the backsheet 23 extend beyond the edges of the absorbent structure 1 to thereby form the periphery of the diaper 20. While the topsheet 21, the backsheet 23, and the absorbent structure 1 may be assembled in a variety of well known configurations, preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715,152, allowed, "Absorbent Article With Dynamic Elastic Waist Feature Having A Predisposed Resilient Flexural Hinge", Kenneth B. Buell et al. filed Jun. 13, 1991; each of which is incorporated herein by reference.

Further embodiments of absorbent structures

FIG. 8 shows a cross-sectional view of an alternative embodiment of the absorbent article 20 along the longitudinal center line 17. The absorbent structure 1 comprises an upper acquisition layer 25, an upper substrate layer 7 to which absorbent gelling material particles 9 are attached, a lower substrate layer 10 to which absorbent gelling material particles 12 are attached. The layer 5 of mixed fibrous material and absorbent gelling material particles forms in this embodiment a central layer and is interposed between the two substrate layers 7,10. FIG. 9 shows the cross-sectional view of the embodiment of FIG. 8 along the transverse centerline 16. As can be seen from this figure, three liquid-distributing channels 40 are formed in the upper layer of absorbent gelling material particles 9 that are attached to the upper substrate 7. The upper channels 40 are preferably 1 cm in width and extend along the length of the absorbent structure 1. A lower channel 42 of a width of 3 cm is formed in the lower layer 12 of absorbent gelling material particles for liquid transport along the bottom of the mixed layer 5 in the direction of the longitudinal center line 17.

FIG. 10 shows a top view of the absorbent structure of FIGS. 8 and 9. The upper substrate 7 comprises four stripes of absorbent gelling material particles 45, the lower substrate 10 comprising two broader stripes 44 of absorbent gelling material particles.

Figure 11:
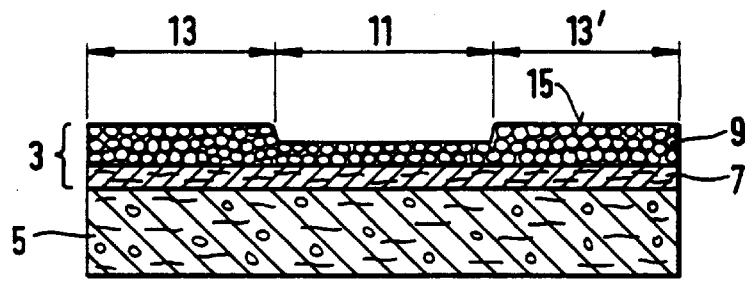

In the embodiment depicted in FIG. 11, the acquisition zone 11 comprises a lower basis weight of absorbent gelling material particles than the storage zones 13,13'. In this embodiment, the substrate 7 is contacting the core 5. An additional fibrous layer or tissue layer is in this case required to be placed on top of the layer of particles 9 to prevent contact between the skin of the user and the particles 9.

Figure 12:
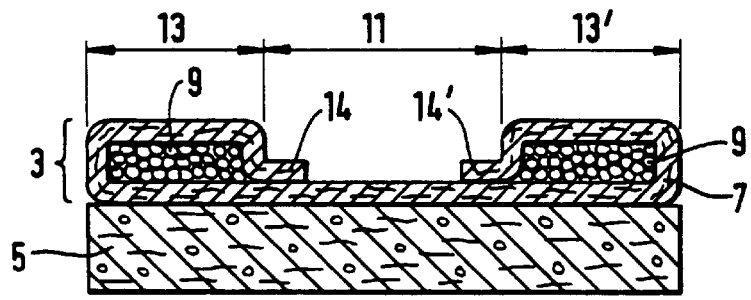

FIG. 12 shows an embodiment wherein the substrate 7 is wrapped around the absorbent gelling material particles 9 and is sealed to itself in doubled-over sections 14,14'. Two chambers are formed, encasing the absorbent gelling material in the storage zone s 13,13'. The advantage of this embodiment is that upon wetting of the absorbent gelling material particles in the storage zone s 13,13', these cannot expand into the acquisition zone 11 as they are restrained by the substrate 7. Hence the acquisition zone 11 remains permeable to liquid in the wet state of the absorbent structure.

Figure 13:
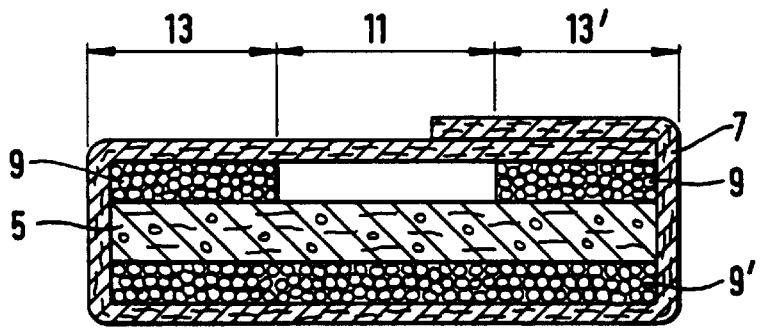
Figure 14:
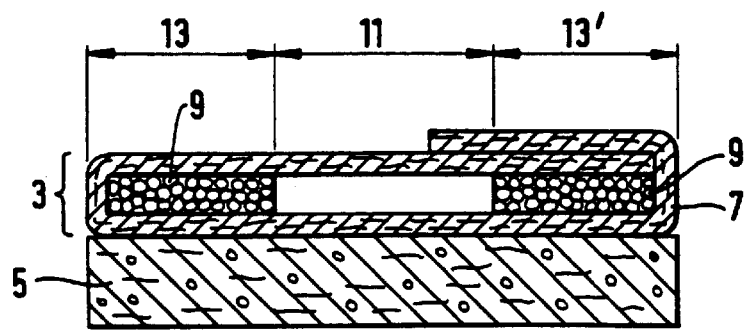

FIG. 13 show an embodiment wherein a single substrate 7 is wrapped around the central mixed layer 5 such that an integral multilayer absorbent structure 1 is formed. FIG. 14 shows an embodiment wherein the layer of particles 9 is enclosed by the substrate 7. In this embodiment the particles 9 are confined to the space enclosed by the substrate 7 and cannot migrate into the layer 5. The laminate formed by the substrate 7 and the particles 9 as shown in FIG. 14, can be formed off line from the manufacturing process of an absorbent article and can be stored on a roll. The absorbent gelling material particles 9 are protected during storage and transport against mechanical damage by the substrate 7. Upon formation of the absorbent structure according to the invention, the laminate 3 can be unwound from the storage roll, and can be combined with the mixed layer 5.

In all of the previously described embodiments, the absorbent gelling material particles in the mixed layer and in the laminates may be of the same chemical or physical structure. However, for the absorbent gelling material particles which are closest to the user-facing side 15 of the absorbent structure it is advantageous to use an absorbent gelling material which for instance has a dynamic swelling rate which is lower than the dynamic swelling rate of the absorbent gelling material particles which are located below the particles at the user-facing side. Alternatively, different absorbent gelling materials can be selected for each layer such the Gel Layer Permeability values (GLP) are different. The use a multilayer structure comprising different types of absorbent gelling material particles has been described in detail in European application no.'s 93305150.0 (attorney's docket CM 580) and 93309614.1 (attorney's docket CM643).

In all embodiments, the different layers forming the absorbent structure 1 may be adhesively interconnected by open networks of adhesive, adhesive beads or spiral adhesive patterns for obtaining improved integrity of the absorbent structure.

Detailed example of an absorbent structure

An absorbent structure according to the invention having a configuration similar to that shown in FIG. 6, can be made in the following way:

An 7.8 cm×22.4 cm (3"×9") acquisition layer 25 is formed from 5 g chemically stiffened cellulose fibers as manufactured by the Weyerhaeuser Paper Company, Columbus Miss. The acquisition layer 25 has a basis weight of 295 g/m$^2$ and a density of 0.09 g/cm$^3$.

For the laminate 3, the substrate 7 is formed by a high wet strength tissue of a basis weight of 22.5 g/m$^2$ as produced by Strepp, Kreuzau, Germany under reference NCB. The dimensions of the tissue are rectangular and measure 44.1 cm×10.2 cm To the tissue, two parallel stripes of hot melt adhesive as manufactured by Findley, Roosendaal, the Netherlands, under reference H 2127 were sprayed along the length of the tissue in an open pattern of a basis weight of 0.8 g/m$^2$. The width of the stripes (the storage zones) is 3.65 cm, the width of the spacing between the stripes (the acquisition zone) being 2.9 cm. 3.3 Gram of absorbent gelling material particles as manufactured by Chemische Fabrik Stockhausen GmbH, PO Box 570, 47705 Krefeld, Germany under the reference SXM 100, were deposited onto the tissue and attached to the adhesively coated areas to form the storage zones 13,13'. The average basis weight of the absorbent gelling material particles in the storage zones 13,13' amounts to 103 g/m$^2$.

16 g of airfelt was airlaid onto a forming screen to form a shaped homogeneous fibrous matrix of a total surface area of about 600 cm$^2$. 8.4 Grams of absorbent gelling material particles of the same type as used in the laminate 3 were homogeneously mixed with the upper part of the fibrous matrix. The mixed layer 5 is formed by the upper part of the fibrous matrix and comprises 38% by weight of the fibers comprised in the matrix. The dusting layer 10 is formed by the lower part of the fibrous matrix and comprises 62% of the weight of the fibers in the fibrous matrix. The density of the fiber matrix (excluding the absorbent gelling material particles) is about 0.13 g/cm$^3$.

6.1Grams of fibers and 8.4 grams of absorbent gelling material particles are comprised in the mixed layer 5 such that 58% by weight of the mixed layer 5 is formed by the absorbent gelling material particles. As 3.4 grams of absorbent gelling material particles are comprised in the laminate, the total weight of the absorbent gelling material particles amounts to 193% of the weight of the fibers in the mixed layer 5.

The laminate 3 is placed on top of the mixed layer 5, the absorbent gelling material particles 9 contacting the layer 5. The acquisition layer 25 is placed onto the substrate layer 7 of the laminate 3. The stacked configuration is encased between a liquid pervious topsheet and a liquid impervious backsheet of 25 micrometers thickness, such as produced by BP Chemicals, Wassersburg, Germany.

Method of making an absorbent structure

Figure 15:
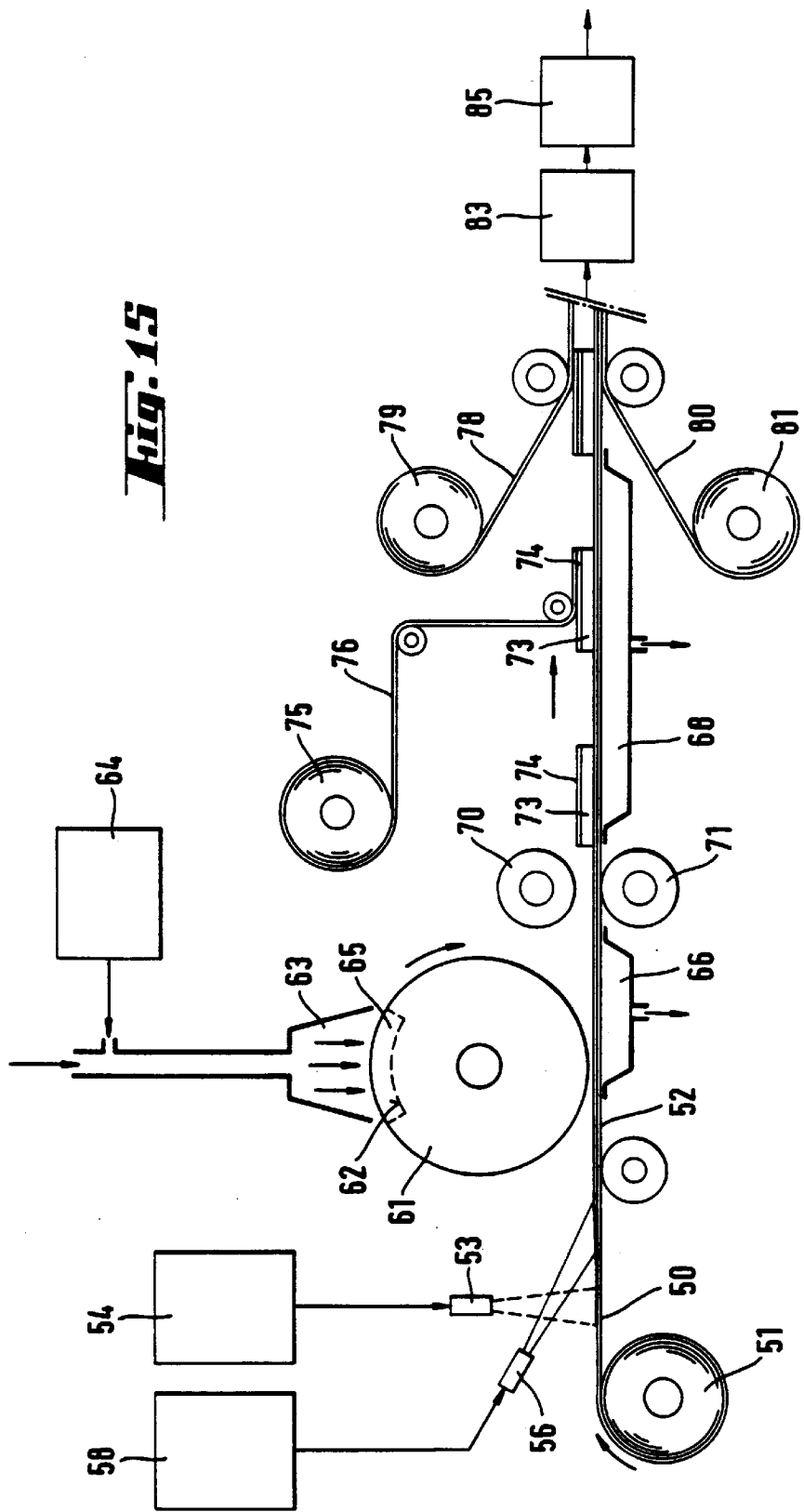

FIG. 15 schematically shows a process of making an absorbent article according to the invention. A first tissue 50 is unwound from a supply roll 51. The tissue 50 forms the user-facing side 15 of the absorbent structure. Hotmelt adhesive is supplied from a tank 54 to a nozzle 53 and is sprayed as meltblown fibers by the nozzle 53 in two longitudinal stripes parallel to the length direction of the tissue 50. Absorbent gelling material particles are supplied from a container 58, and are blown by an airgun 56 through the spray of adhesive exiting from the nozzle 53. The absorbent particles are directed by the airgun 56 onto the same longitudinal parallel stripes of the tissue 50 as the adhesive. The adhesively coated absorbent gelling material particles are depostited in the storage zones of the substrate and form in combination with the tissue, the laminate 52.

Cellulosic fibers are deposited via a chute 63 onto a laydown screen 62 of a rotating laydown drum 61. Absorbent gelling material particles are mixed into the airstream that carries the fibers from a storage container 64. On the laydown drum 61, the mixed layer 73, is formed. The absorbent gelling material particles from the container 64 are introduced in the fiber stream such that they are predominantly located on right-hand side of the chute 63. Hence the fibers that are first deposited onto the laydown screen 62 when the laydown cavity 64 is rotated underneath the chute, are not mixed with absorbent gelling material particles, and form the dusting layer 74. The absorbent element comprising the dusting layer 74 and the mixed layer 73, is placed onto the laminate 52. A suction device 66,68 draws the fibrous absorbent element 73 onto the laminate and maintains the absorbent elements in a defined position.

In a nip formed by a pair of calender rolls 70 and 71, the absorbent elements 73 are compressed to the desired thickness and density. From a further supply roll 75, a pre-formed laminate 76 of the type as shown in FIG. 14, is unwound and is placed on the backsheet-facing side of the absorbent element 73. The use of the pre-formed laminate 76 is optional and can be omitted when only a single laminate is desired at the user-facing side of the absorbent structure. Alternatively, the backsheet-facing laminate 76 can be made in an on-line manner similar to the way in which the laminate 52 is formed. Then the backsheet 78 and topsheet 80 are supplied from supply rolls 79 and 81 respectively, and are combined with the absorbent element 73 which now comprises the backsheet-facing laminate 76, the dusting layer 74, the mixed layer 73 and the topsheet-facing laminate 52. The continuous band of absorbent articles is then cut to form individual absorbent articles in a cutting unit which has not been depicted in this figure. The individual absorbent articles are folded in a folding unit 83 and are stacked, compressed and packed in a packing unit 85.

By using relatively low concentrations of absorbent gelling material for the formation of the mixed layer on the laydown drum 61, the absorbent gelling material particles are retained firmly within the fibrous matrix. Loss of absorbent gelling material particles from the fibrous matrix is reduced in the process at the stages of:

Laydown of the fibers and absorbent gelling particles onto the rotating drum 61. Especially at high rates of formation of absorbent structures, the absorbent gelling material particles are subject to rotational forces which tend to dislocate the particles within or away from the fibrous matrix and which can eject the particles from the laydown cavity 64.

The trajectory between the laydown drum 61 and the calender nip formed by rolls 70,71. Before compression of the mixed layer, the retention of the particles in the fibrous matrix is lower than after compression. Hence the tendency of the particles to shift within or to be separated from the mixed layer is relatively large before calendering of the mixed layer between the rolls 70,71.

In the folding unit 83 and in the packing unit 85, the absorbent articles are subject to a relatively large number of movements which tend to separate the particles form the fibers.

The use of low concentrations of absorbent gelling material particles in the mixed layer at the above process stages results in reduced loss of particles, less contamination of the process equipment and more efficient use of absorbent gelling material.

The process for forming the absorbent article according to the invention has only schematically been described. The process steps of attachment of elastic elements and provision of a tape fastening system have been omitted. A detailed description of a process for forming a mixed layer has been described in U.S. Pat. Nos. 4,765,780 and 4,764,325 (Angstadt).

Test Methods

All tests are carried out at about 23°±2° C. and at 50±10% relative humidity.

The specific synthetic urine used in the test methods is commonly known as Jayco SynUrine and is available from Jayco Pharmaceuticals Company of Camp Hill, Pa. The formula for the synthetic urine is: 2.0 g/l of KCl; 2.0 g/l $Na_2SO_4$; 0.85 g/l of $(NH_4) H_2PO_4$; 0.15 g/l $(NH_4)_2HPO_4$; 0.19 g/l of $CaCl_2$; and 0.23 g/l of $MgCl_2$. All of the chemicals are of reagent grade. The pH of the synthetic urine is in the range of 6.0 to 6.4.

The sample pads are prepared using a padmaker machine, such as is described below or an equivalent machine, which provides a consistent and homogeneous laydown of fluff.

Figure 16:
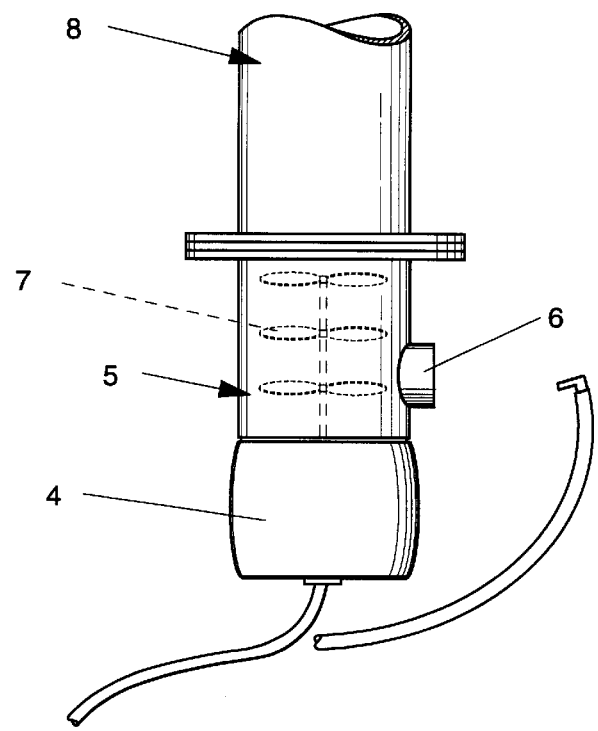
FIG. 16 is a side view of an air laid felt padmaker machine used to make the sample pads for the Wet Compressibility and Drip Capacity tests.
Figure 17:
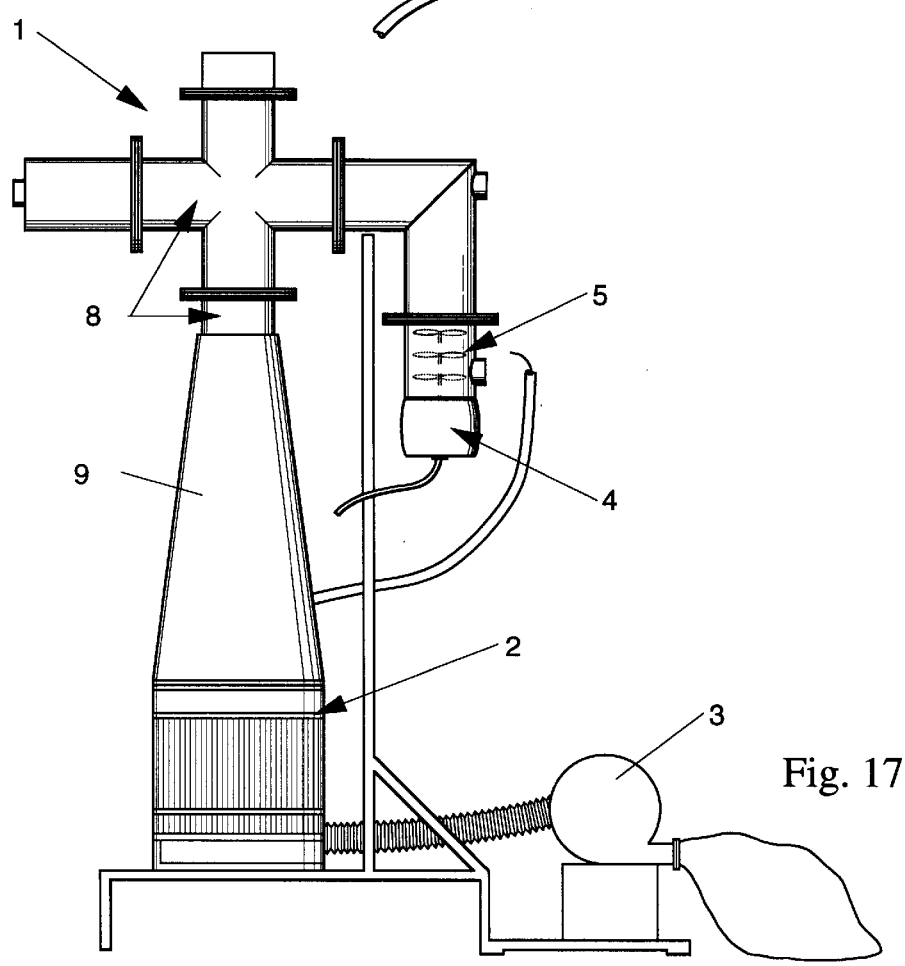
FIG. 17 is an enlarged view of a portion of FIG. 16.

Referring to FIGS. 16 and 17, four 30 g portions of dry fluff (or equivalent material, for example chemically cross-linked cellulose) are weighed out. A ply of tissue porous enough for air to pass through it while retaining fluff on it, is cut to 36.8 cm×36.8 cm (14.5 in.×14.5 in.) and is placed evenly on the forming screen (2) of an air laid felt padmaker machine (1). The tissue (not shown) completely covers the forming screen and is made to curve up at its sides to prevent escape of the fluff. The tissue forms the bottom of the pad. The vacuum (3), chamber motor (4) and compressed air supply on the padmaker machine are turned on. One 30 g portion of fluff is added to the sample chamber (5) on the padmaker machine in small amounts via the sample feed (6) and without obstructing the blades (7) of the machine. Compressed air is circulated vigorously in the chamber to expedite separation and passage of the fibers through the plexiglass® cylinder (8) and the prismoid column (9) to the forming screen (2).

The vacuum (3) is turned off and the forming screen (2) is pulled out of the padmaker machine (1) and rotated through a quarter turn in the clockwise direction. The screen is returned to the padmaker machine. Another 30 g portion of fluff is added to the chamber (5) on the machine and the above procedure is repeated. Fluff is added in the same manner until all four portions have been transferred to the forming screen. The forming screen, and the pad formed thereon, is then removed from the padmaker machine, and the pad is carefully transferred from the screen to a piece of cardboard, or similar smooth flat surface. A second ply of tissue is added to the top of the pad, and a second piece of cardboard placed on top of that.

A steel weight having dimensions of around 35.6 cm×35.6 cm×2.5 cm (14 in.×14 in.×1 in.) having a weight of around 16.3 kg (36 lbs) is placed on top of the pad for approximately 120 seconds, or longer until the pad is needed. The weight is then removed and the pad is pressed by application of a force of around 4,500 kg (10,000 lbs) on a large Carver press to improve pad integrity. The pad is removed from the press and trimmed on a paper cutter to have dimensions around 30.5 cm×30.5 cm (12 in.×12 in.), and is then further cut according to the size required by the particular test in which it is to be used.

The use of a padmaker machine to form the sample pads is not intended to be limiting. Any suitable method can be used provided a consistent and homogeneous laydown of fluff is achieved, which is then compressed under the above conditions to give a pad having substantially the same density and basis weight as achieved above.

1. Wet Compressibility Test

This test is designed to measure the volume of a pad of fibrous material under varying load conditions when wet. The objective is to measure the fibrous material's resistance to load by measuring the volume maintained under that load.

A fluff test pad is prepared as described above. Any tissue present on the surfaces of the pad is removed. The pad is then densified under a 3.6 kg $cm^{-2}$ (51 psi) load for pad integrity reasons using a Carver laboratory press. The thickness of the pad is measured and its fiber density calculated by pad weight÷(pad thickness×pad area).

The dry weight of the pad is multiplied by 10, and this represents the target wet weight on loading. The dry pad is transferred onto a top loading balance having a 0.01 g sensitivity. Synthetic urine is dispensed slowly onto the pad until the target wet weight is achieved as measured by the balance. The wet pad is carefully transferred onto the surface of a compressibility tester of the Buckeye design, and a weight having substantially the same area as the pad (about 10.2 cm×10.2 cm) and corresponding to a pressure of 77 g cm$^{-2}$ (1.1 psi) is lowered slowly onto the pad. The pad is left for 60 seconds to allow it to equilibrate under the load, and then the thickness of the compressed pad is recorded using calipers.

The Wet Compressibility is the void volume per gram of dry fluff and is calculated as follows:

Void Volume (cm$^3$)=Total Volume−Fiber Volume=(pad thickness under load (cm)×pad area (cm$^2$))−(pad dry weight (g)/fiber density (g cm$^{-3}$))

Wet Compressibility=Void volume per gram=÷pad dry wt. (g)

where fiber density is calculated from the initial pad weight and thickness measurements (i.e. under no load conditions).

2. Drip Capacity Test

A sample pad prepared as described above is cut on a paper cutter to have dimensions 7.5 cm×7.5 cm. The pad is weighed and is placed on a large mesh wire screen which is in turn positioned on a drip tray. The whole apparatus is then mounted on a top-loading balance.

Synthetic urine is introduced via a pump (Model 7520-00, as supplied by Cole-Parmer Instruments Company, Chicago, USA) into the center of the sample pad at a rate of 5±0.25 ml s$^{31}$ $^1$. The time for the pad to release the first drop of synthetic urine through the bottom of the pad and into the drip tray is recorded. The pump is immediately stopped as soon as this occurs. The time recorded and the pumping rate are then used to calculate the volume (ml) of synthetic urine absorbed by the sample on reaching saturation, i.e. when the sample starts to drip. (The balance can be used to check this periodically, thereby minimizing any variation in the pump delivering the synthetic urine.) This is referred to as the Drip Capacity, and is given as the ratio:

Urine retained by sample pad on saturation (ml)÷Dry weight of sample (g)

What is claimed is:

1. Absorbent structure comprising an upper layer and a lower layer, each layer comprising absorbent gelling material particles, the upper layer comprising an acquisition zone and a storage zone, the average basis weight of absorbent gelling material particles in the acquisition zone being lower than the average basis weight of the absorbent gelling material particles in the storage zone, wherein the lower layer comprises a mixture of absorbent gelling material particles and fibers, wherein the upper layer comprises a liquid-permeable substrate and a layer of absorbent gelling material particles attached to said substrate, the weight of the absorbent gelling material particles in the mixed lower layer being not more than 70 percent, of the weight of the mixed lower layer, the combined weight of absorbent gelling material particles in the upper layer and in the mixed lower layer being at least 80 percent, of the weight of fibers in the mixed lower layer.

2. Absorbent structure comprising an upper layer and a lower layer, each layer comprising absorbent gelling material particles, wherein the upper layer comprises a mixture of absorbent gelling material particles and fibers, the weight of the absorbent gelling material particles in the mixed upper layer being not more than 70 percent, of the weight of the mixed upper layer, the lower layer comprising a substrate, the layer of absorbent gelling material particles of the lower layer being attached to said substrate, wherein the combined weight of absorbent gelling material particles in the mixed upper layer and in the lower layer is at least 80 percent of the weight of the fibers in the mixed upper layer.

3. Absorbent structure according to claim 1, the structure comprising a bottom layer comprising a substrate and absorbent gelling material particles attached to said substrate.

4. Absorbent structure according to claim 2, the structure comprising a top layer comprising a substrate and absorbent gelling material particles attached to said substrate, the top layer comprising an acquisition zone and a storage zone, the average basis weight of absorbent gelling material particles in the acquisition zone being lower than the average basis weight of the absorbent gelling material particles in the storage zone.

5. Absorbent structure according to claim 1, wherein a fibrous layer, substantially free of absorbent gelling material particles, is located adjacent and below the mixed layer.

6. Absorbent structure according to claim 1, wherein, the acquisition zone comprises a stripe which is substantially free of absorbent gelling material particles.

7. Absorbent structure according to claim 1, wherein the mixed layer comprises a substantially homogeneous mixture of absorbent gelling material particles and fibers.

8. Absorbent structure according to claim 1, wherein the absorbent gelling material particles that are attached to the substrate layer form an interpartically crosslinked macro-structure.

9. Absorbent structure according to claim 1 wherein the substrate comprises a tissue, the absorbent gelling material particles that are attached to the substrate being wrapped in said tissue.

10. Absorbent structure according to claim 1 wherein the substrate is adhesively connected to the layer that is located adjacent the substrate.

11. Absorbent structure according to claim 1 wherein the substrate enwraps the layer comprising the mixture of fibers and absorbent gelling material particles.

12. Absorbent structure according to claim 1, wherein the average basis weight of the absorbent gelling material in storage zone of the upper layer is at least 25 g/m$^2$.

13. Absorbent structure according to claim 1 wherein the upper layer is covered by an acquisition layer.

14. Absorbent structure according to claim 13, wherein the acquisition layer has a wet compressibility of at least 5 cm$^3$g$^{-1}$ of and a drip capacity of at least 10 gg$^{-1}$.

15. Absorbent structure according to claim 4, wherein the bottom layer comprises at least one liquid-directing channel for promotion of longitudinal liquid migration.

16. Absorbent article comprising a liquid-permeable topsheet, a liquid-impermeable backsheet and an absorbent structure according to claim 1, interposed between the topsheet an d the backsheet.

17. Absorbent article according to claim 16, the caliper of the absorbent article being below 8.4 cm (3.3 inches) in a stack height test comprising 10 bi-folded articles.

18. Method of making an absorbent structure the method comprising the steps of:

providing a liquid-pervious substrate and absorbent gelling material particles attached to said substrate providing an airstream of fibers, introducing absorbent gelling materials into said airstream, laying down a mixture of fibers and particles onto a forming screen to form a mixed layer, and combining the mixed layer and the laminate to form an absorbent structure according to claim 1.

19. Method according to claim 18, the method further comprising the steps of:
depositing absorbent gelling material particles onto the substrate and
attaching the particles to the substrate.

20. Method according to claim 19, wherein the absorbent gelling material paritlces are directed through a stream of adhesive prior to contacting the substrate to form adhesively coated particles, followed by depositing the adhesively coated particles onto the substrate.

21. Absorbent structure according to claim 1 wherein the weight of the absorbent gelling material particles in the mixed lower layer being not more than 60 percent of the weight of the mixed lower layer, the combined weight of absorbent gelling material particles in the upper layer and in the mixed lower layer being at least 80 percent of the weight of fibers in the mixed lower layer.

22. Absorbent structure according to claim 21 wherein the weight of the absorbent gelling material particles in the mixed lower layer being not more than 70 percent of the weight of the mixed lower layer, the combined weight of absorbent gelling material particles in the upper layer and in the mixed lower layer being at least 140 percent of the weight of fibers in the mixed lower layer.

23. Absorbent structure according to claim 22 wherein the weight of the absorbent gelling material particles in the mixed lower layer being not more than 60 percent of the weight of the mixed lower layer, the combined weight of absorbent gelling material particles in the upper layer and in the mixed lower layer being at least 140 percent of the weight of fibers in the mixed lower layer.

24. Absorbent structure according to claim 2 wherein the upper layer comprises a mixture of absorbent gelling material particles and fibers, the weight of the absorbent gelling material particles in the mixed upper layer being not more than 60 percent of the weight of the mixed upper layer, the lower layer comprising a substrate, the layer of absorbent gelling material particles of the lower layer being attached to said substrate, wherein the combined weight of absorbent gelling material particles in the mixed upper layer and in the lower layer is at least 80 percent of the weight of the fibers in the mixed upper layer.

25. Absorbent structure according to claim 24 wherein the upper layer comprises a mixture of absorbent gelling material particles and fibers, the weight of the absorbent gelling material particles in the mixed upper layer being not more than 70 percent of the weight of the mixed upper layer, the lower layer comprising a substrate, the layer of absorbent gelling material particles of the lower layer being attached to said substrate, wherein the combined weight of absorbent gelling material particles in the mixed upper layer and in the lower layer is at least 140 percent of the weight of the fibers in the mixed upper layer.

26. Absorbent structure according to claim 25 wherein the upper layer comprises a mixture of absorbent gelling material particles and fibers, the weight of the absorbent gelling material particles in the mixed upper layer being not more than 60 percent of the weight of the mixed upper layer, the lower layer comprising a substrate, the layer of absorbent gelling material particles of the lower layer being attached to said substrate, wherein the combined weight of absorbent gelling material particles in the mixed upper layer and in the lower layer is at least 140 percent of the weight of the fibers in the mixed upper layer.

27. Absorbent structure according to claim 12, wherein the average basis weight of the absorbent gelling material in storage zone of the upper layer is at least 40 g/m$^2$.

* * * * *

UNITED STATES PATENT AND TRADEMARK OFFICE
CERTIFICATE OF CORRECTION

PATENT NO.    : 5,830,202
DATED         : November 3, 1998
INVENTOR(S)   : Bogdanski et al.

It is certified that error appears in the above-identified patent and that said Letters Patent is hereby corrected as shown below:

Column 4,
Line 8, please delete "preformed" and insert therefor -- pre-formed --.

Column 9,
Line 2, please delete "10 $gg^{-1}$" and insert therefor -- 10 g $g^{-1}$ --.
Line 2, please delete "3in" and insert therefor -- in --.
Line 64, please delete "081142258" and insert therefor -- 08/142258 --.

Column 13,
Line 2, please delete "zone s" and insert thereof -- zones --.
Line 14, please delete "zone s" and insert thereof -- zones --.

Column 16,
Line 25, please delete "30 g" and insert therefor -- 30g --.

Column 17,
Line 28, please delete "ml $s^{31\ 1}$" and insert therefor -- ml $s^{-1}$ --.
Line 54, after "percent" please delete "," (the comma).
Line 58, after "percent" please delete "," (the comma).
Line 66, after "percent" please delete "," (the comma).

Signed and Sealed this

Thirty-first Day of December, 2002

JAMES E. ROGAN
*Director of the United States Patent and Trademark Office*

UNITED STATES PATENT AND TRADEMARK OFFICE
CERTIFICATE OF CORRECTION

PATENT NO. : 5,830,202
DATED : November 3, 1998
INVENTOR(S) : Bogdanski et al.

It is certified that error appears in the above-identified patent and that said Letters Patent is hereby corrected as shown below:

Column 18,
Line 21, after "wherein" delete ",".
Lines 31, 35, 38 and 44, after "claim 1" insert -- , --.
Line 55, delete "an d" and insert -- and --.

Column 19,
Line 9, delete "paritlces" and insert -- particles --.

Signed and Sealed this

Third Day of January, 2006

JON W. DUDAS
*Director of the United States Patent and Trademark Office*